(12) United States Patent
Rubinstenn et al.

(10) Patent No.: US 6,761,697 B2
(45) Date of Patent: Jul. 13, 2004

(54) METHODS AND SYSTEMS FOR PREDICTING AND/OR TRACKING CHANGES IN EXTERNAL BODY CONDITIONS

(75) Inventors: Gilles Rubinstenn, Paris (FR); Francis Pruche, Senlis (FR)

(73) Assignee: L'Oreal SA (FR)

( * ) Notice: Subject to any disclaimer, the term of this patent is extended or adjusted under 35 U.S.C. 154(b) by 0 days.

(21) Appl. No.: 10/024,354

(22) Filed: Dec. 21, 2001

(65) Prior Publication Data

US 2003/0065278 A1 Apr. 3, 2003

Related U.S. Application Data

(60) Provisional application No. 60/325,559, filed on Oct. 1, 2001.

(51) Int. Cl.⁷ .......................... A61B 5/103; A61B 5/117
(52) U.S. Cl. ....................................... 600/587
(58) Field of Search .................. 600/587, 300, 600/407; 514/63, 725; 382/128, 276, 154, 100; 705/1, 26, 10; 358/1.9; 434/377, 99; 706/48

(56) References Cited

U.S. PATENT DOCUMENTS

| | | | |
|---|---|---|---|
| 4,826,828 A | * | 5/1989 | Wilmott et al. ............... 514/63 |
| 5,751,829 A | | 5/1998 | Ringland et al. |
| 6,091,836 A | | 7/2000 | Takano et al. |
| 6,260,024 B1 | | 7/2001 | Shkedy |
| 6,293,284 B1 | | 9/2001 | Rigg |
| 2001/0011818 A1 | | 8/2001 | Dockery et al. |
| 2001/0014868 A1 | | 8/2001 | Herz et al. |
| 2001/0017936 A1 | | 8/2001 | Loussouarn et al. |
| 2002/0024528 A1 | | 2/2002 | Lambertsen |
| 2002/0054714 A1 | | 5/2002 | Hawkins et al. |

FOREIGN PATENT DOCUMENTS

| | | |
|---|---|---|
| EP | 0 226 959 | 7/1987 |
| EP | 1 030 267 | 8/2000 |
| EP | 1 134 701 | 9/2001 |
| EP | 1 169 964 | 1/2002 |

(List continued on next page.)

OTHER PUBLICATIONS

Yin Wu, et al., "A Plastic–Visco–Elastic Model for Wrinkles in Facial Animation and Skin Aging", MIRALab, 1998.

Catherine Pelachaud, et al., "Final Report to NSF of the Standards for Facial Animation Workshop", The Institute For Research In Cognitive Science, Unversity of Pennsylvania, IRCS Report 94–21, Nov. 1994, pp. 1–62.

Copending application No. 10/024,354; Title: Body Image Enhancement, Inventor(s): Gilles Rubinstenn et al. U.S. filing Date: Dec. 21, 2001, Preliminary Amendment Filed: Apr. 22, 2002.

(List continued on next page.)

*Primary Examiner*—Max F. Hindenburg
*Assistant Examiner*—Brian Szmal
(74) *Attorney, Agent, or Firm*—Finnegan, Henderson, Farabow, Garrett & Dunner, LLP

(57) ABSTRACT

The present invention includes a method for predicting evolution of at least one condition of an external body portion of a subject. The method may include receiving first data, receiving second data, generating a forecasted or expected evolution of the at least one condition of the external body portion of the subject based on the first data and the second data, and transmitting to the subject the forecasted evolution. The first data may be representative of at least one condition of the external body portion of the subject in a first time frame. The second data may be representative of the at least one condition of the external body portion of the subject in a second time frame occurring after the first time frame. A beauty product may be applied to the external body portion between the first and second time frames.

56 Claims, 12 Drawing Sheets

FOREIGN PATENT DOCUMENTS

| WO | WO 98/20458 | 5/1998 |
| --- | --- | --- |
| WO | WO 99/23609 | 5/1999 |
| WO | WO 01/04840 | 1/2000 |
| WO | WO 00/33271 | 6/2000 |
| WO | WO 00/76398 | 12/2000 |
| WO | WO 01/04838 | 1/2001 |
| WO | WO 01/18674 | 3/2001 |
| WO | WO 01/20517 | 3/2001 |
| WO | WO 01/57771 | 8/2001 |
| WO | WO 01/80122 | 10/2001 |
| WO | WO 01/779976 | 10/2001 |
| WO | WO 01/87245 | 11/2001 |
| WO | WO 01/91600 | 12/2001 |
| WO | WO 01/91601 | 12/2001 |
| WO | WO 02/03232 | 1/2002 |
| WO | WO 02/05249 | 1/2002 |
| WO | WO 02/37421 | 5/2002 |
| WO | WO 02/082350 | 10/2002 |

OTHER PUBLICATIONS

Co–pending application No. 10/024,333; Title: Methods and Systems for Generating a Prognosis, Inventor(s): Gilles Rubinstenn et al. U.S. filing Date: Dec. 21, 2001, Preliminary Amendment Filed: Apr. 22, 2002.

Copending application No. 10/024,622; Title: Historical Beauty Record, Inventor(s): Daniela Giacchetti et al., U.S. filing Date: Dec. 21, 2001, Preliminary Amendment Filed: Apr. 22, 2002.

Co–pending application No. 10/024,332; Title: Indentification and Presentation of Analogous Beauty Case Histories, Inventor(s): Gilles Rubinstenn, U.S. filing Date: Dec. 21, 2001, Preliminary Amendment Filed: Apr. 22, 2002.

Co–pending application No. 10/024,481; Title: Interactive Beauty Analysis, Inventor(s): Gilles Runinstenn et al., U.S. filing Date: Dec. 21, 2001, Preliminary Amendment Filed: Apr. 22, 2002.

Co–pending application No. 10/024,495; Title: Feature Extraction in Beauty Analysis, Inventor(s): Gilles Rubinstenn et al., U.S. filing Date: Dec. 21, 2001, Preliminary Amendment Filed: Apr. 22, 2002.

Co–pending application No. 10/024,353; Title: Simulation of an Aesthetic Feature on a Facial Image, Inventor(s): Daniela Giacchetti et al., U.S. filing Date: Dec. 21, 2001, Preliminary Amendment Filed: Apr. 22, 2002.

Co–pending application No. 10/024,496; Title: Beauty Advisory System and Method, Inventor(s): Gilles Rubinstenn et al., U.S. filing Date: Dec. 21, 2001, Preliminary Amendment Filed: Apr. 22, 2002.

Co–pending application No. 10/024,620; Title: Virtual Beauty Consultant, Inventor(s): Daniela Giacchetti et al., U.S. filing Date: Dec. 21, 2001, Preliminary Amendment Filed: Apr. 22, 2002.

Co–pending application No. 10/024,334; Title: Calibrating Image Capturing, Inventor(s): Gilles Rubinstenn, U.S. filing Date: Dec. 21, 2001, Preliminary Amendment Filed: Apr. 22, 2002.

Co–pending application No. 10/024,616; Title: Use of Artificial Intelligence in Providing Beauty Advice, Inventor(s): Jerome Peyrelevade, U.S. filing Date: Dec. 21, 2001, Preliminary Amendment Filed: Apr. 22, 2002.

Co–pending application No. 10/024,352; Title: Shop–In–Shop Website Construction, Inventor(s): Jerome Peyrelevade et al., U.S. filing Date: Dec. 21, 2001.

Co–pending application No. 10/024,619; Title: Early Detection of Beauty Treatment Progress, Inventor(s): Francis Pruche et al., U.S. filing Date: Dec. 21, 2001, Preliminary Amendment Filed: Apr. 22, 2002.

Co–pending application No. 10/024,356; Title: Cosmetic Affinity Indexing, Inventor(s): Daniela Giacchetti et al., U.S. filing Date: Dec. 21, 2001.

Co–pending application No. 10/024,621; Title: Systems and Methods for Providing Beauty Guidance, Inventor(s): Daniela Giacchetti et al., U.S. filing Date: Dec. 21, 2001, Preliminary Amendment Filed: Apr. 22, 2002.

Co–pending application No. 10/024,355; Title: Methods and Systems Involving Simulated Application of Beauty Product, Inventor(s): Jerome Peyrelevade et al., U.S. filing Date: Dec. 21, 2001, Preliminary Amendment Filed: Apr. 22, 2002.

Co–pending application No. 10/024,351; Title: Customized Beauty Tracking Kit, Inventor(s): Gilles Rubinstenn et al., U.S. filing Date: Dec. 21, 2001, Preliminary Amendment Filed: Apr. 22, 2002.

Co–pending application No. 10/024,615; Title: Analysis Using a Three–Dimensional Facial Image, Inventor(s): Gilles Rubinstenn et al., U.S. filing Date: Dec. 21, 2001, Preliminary Amendment Filed: Apr. 22, 2002.

Co–pending application No. 10/024,482; Title: Body Image Templates with Pre–Applied Beauty Products, Inventor(s): Daniela Giacchetti, U.S. filing Date: Dec. 21, 2001, Preliminary Amendment Filed: Apr. 22, 2002.

Co–pending application No. 10/024,651; Title: Image Capture Method, Inventor(s): Gilles Rubinstenn, U.S. filing Date: Dec. 21, 2001, Preliminary Amendment Filed: Apr. 22, 2002.

Co–pending application No. 10/024,034; Title: Devices and Methods for Enabling Evaluation of Typological Characteristics of External Body Portions, and Related Devices, Inventor(s): Roland Bazin, U.S. filing Date: Dec. 21, 2001.

English Abstract of KR 20010067927.

* cited by examiner

QUANTITY = 100
AVG. INTENSITY = 70%
AVG. SIZE = 1.00 MM

QUANTITY = 101
AVG. INTENSITY = 70%
AVG. SIZE = 1.01 MM

QUANTITY = 99
AVG. INTENSITY = 70%
AVG. SIZE = 0.99 MM

MONTH 0:

400

QUANTITY = 100
AVG. INTENSITY = 70%
AVG. SIZE = 1.00 MM

FIG. 10A

MONTH 6:

500

QUANTITY = 101
AVG. INTENSITY = 70%
AVG. SIZE = 1.01 MM

FIG. 10B

MONTH 18:

600

QUANTITY = 105
AVG. INTENSITY = 70%
AVG. SIZE = 1.05 MM

FIG. 10C

MONTH 66:
1010

QUANTITY = 125
AVG. INTENSITY = 75%
AVG. SIZE = 1.10 MM

FIG. 10D

WEEKLY USE OF
FRECKAWAY CREAM

800

QUANTITY = 99
AVG. INTENSITY = 70%
AVG. SIZE = 0.99 MM

FIG. 10E

WEEKLY USE OF
FRECKAWAY CREAM
1020

QUANTITY = 100
AVG. INTENSITY = 70%
AVG. SIZE = 1.00 MM

FIG. 10F

DAILY USE OF
FRECKAWAY CREAM

1030

QUANTITY = 95
AVG. INTENSITY = 70%
AVG. SIZE = 0.97 MM

FIG. 10G

DAILY USE OF
FRECKAWAY CREAM

1040
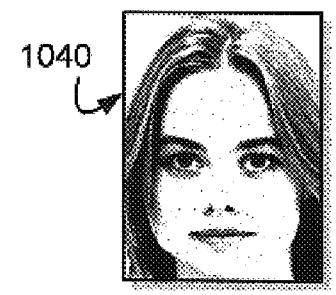

QUANTITY = 90
AVG. INTENSITY = 65%
AVG. SIZE = 0.90 MM

FIG. 10H

METHODS AND SYSTEMS FOR PREDICTING AND/OR TRACKING CHANGES IN EXTERNAL BODY CONDITIONS

This application claims priority to U.S. provisional application No. 60/325,559, filed Oct. 1, 2001.

BACKGROUND OF THE INVENTION

1. Field of the Invention

The present invention involves methods and systems for predicting and/or tracking changes of one or more conditions of an external body portion of a subject. The invention may have applicability in predicting future evolution of one or more external body conditions. The invention may also have particular use with gauging and/or predicting effectiveness of beauty products applied to the external body portion.

2. Description of Related Art

Individuals always have a curiosity in learning about what will happen in the future. One particular area of interest relates to an individual's curiosity about how she will look in the future. Since a "crystal ball" or "time machine" exist only in fairy tales and science fiction, an exact forecast of an individual's future appearance is impossible to attain. With the advancement of modern research techniques and data processing devices, however, somewhat accurate assessments of an individual's prognosis are becoming more and more possible.

One area where there is a particular interest in using information relating to an individual's future outlook is in the field of beauty products. For example, a large number of beauty products are useful to combat signs of aging. As an individual grows older, she may develop conditions such as wrinkles, skin lines, hair loss, and skin discolorations, such as those caused by over-exposure to the sun. Using available beauty products, at least some of these conditions may be eliminated, reduced, or slowed to a less aggressive pace. However, beauty products are typically only used when an individual senses aggressive onset of a visibly perceptible symptom. Less common is the use of beauty products as a preventative measure, which is sometimes the most effective way of improving someone's future outlook.

For example, it's generally known that using sun screen products may reduce the number and intensity of wrinkles appearing later in a person's life. Even with such a well know fact, individuals rarely look that far into the future and apply sun screen just to prevent the onset of wrinkles ten or fifteen years later. Furthermore, it's even rarer for an individual to apply sun screen at optimum strengths and/or usage levels because most individuals are not that far-thinking.

Enabling consumers to understand the future outlook of the their personal appearance would be particularly advantageous for purveyors of beauty products. For example, making individuals aware of how much better they might look in the future if they use certain beauty products earlier in their life would provide a means to encourage individuals to purchase a greater number those products and to use them throughout their life.

SUMMARY OF A FEW ASPECTS OF THE INVENTION

Methods and systems consistent with the features and principles of the present invention may be used in predicting future changes to external body conditions and/or tracking changes that have already occurred.

One exemplary aspect of the invention may include a method for predicting evolution of one or more conditions of an external body portion of a subject. The method may include receiving first data and receiving second data. The first data may be representative of one or more conditions of the subject's external body portion in a first time frame, and the second data may be representative of the condition of the subject's external body portion in a second time frame occurring after the first time frame. Alternatively, the second data may be reflective of how the at least one external condition is expected to evolve over time. The method may further include generating a forecasted evolution of the condition and transmitting the forecasted evolution to the subject. The generation of the forecasted evolution may be based on the first data and the second data. The forecasted evolution could be in a variety of differing forms, such as images, diagrams, graphs, charts, and other representations.

In another exemplary aspect, the method may include receiving third, fourth, or additional data. These data may be data relating to the condition in time periods falling prior to, after, or between the time periods of the first and second data.

Yet another exemplary aspect of the invention may include a method for enabling a subject to gauge effectiveness of one or more one beauty products. The method may include receiving first data and receiving second data. The first data may be representative of one or more conditions of an external body portion of a subject in a first time frame, and the second data may be representative of the condition of the external body portion of the subject in a second time frame occurring after the first time frame. At least one beauty product may be applied to the external body portion between the first time frame and the second time frame. The method may also involve generating evolution data based at least in part on the first and second data, presenting to the subject a first representation of the evolution data, and presenting to the subject a second representation of an expected evolution of the at least one condition in conjunction with the first representation. The conjunctive presentation of the first and second representations may be configured to permit the subject to gauge effectiveness of the beauty product applied between the first and second time frames.

Still another exemplary aspect of the invention may include generating expected evolution predicting affects of varying usage of beauty products.

Additional aspects of the invention are set forth in the description which follows, and in part will be apparent from the description, or may be learned by practice of methods and articles consistent with features of the present invention.

It is understood that both the foregoing description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several aspects of the invention and together with the description, serve to explain principles of the invention. In the drawings.

FIGS. 10A–10H illustrate exemplary time-lapsed images conjunctively presenting forecasted and expected evolutions consistent with features and principles of the invention;

DESCRIPTION OF EXEMPLARY EMBODIMENTS

Reference is now made in detail to embodiments consistent with the invention, examples of which are illustrated in the accompanying drawings. Wherever possible, the same reference numbers may be used throughout the drawings to refer to the same or like parts.

Figure 1:
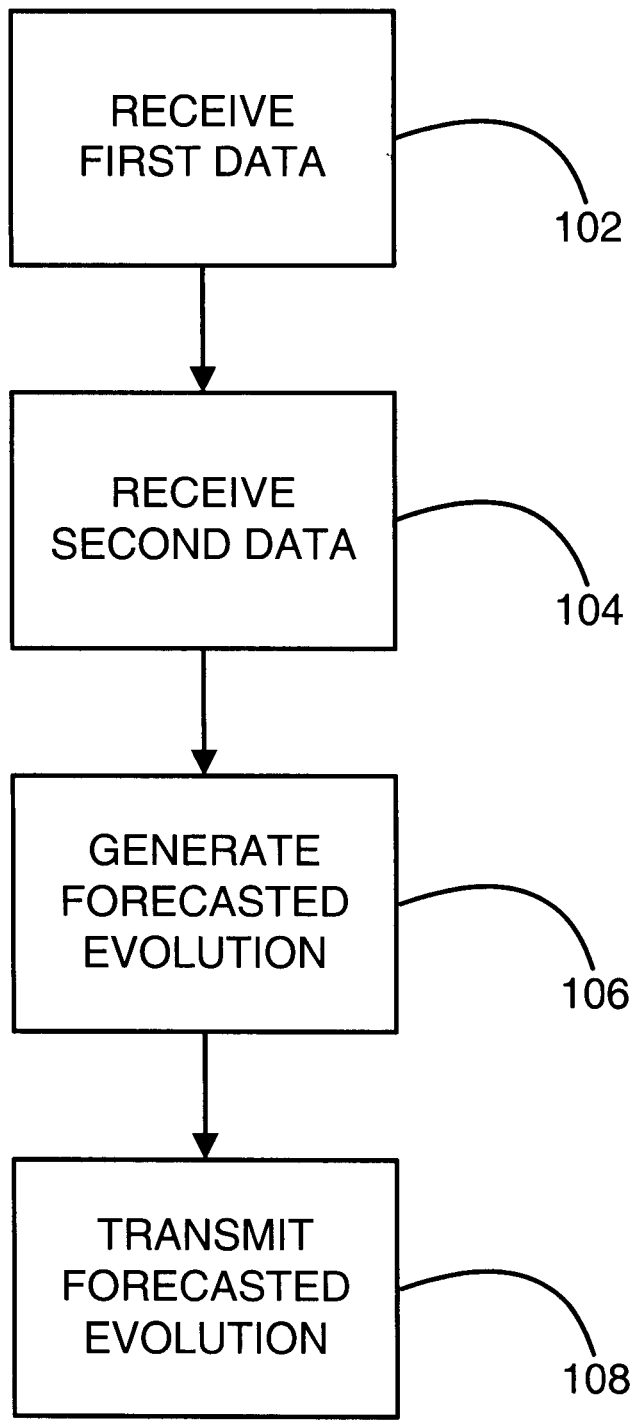
FIG. 1 illustrates a first exemplary flowchart consistent with features and principles of the invention.

The present invention may include a method for predicting evolution of at least one condition of an external body portion of a subject. FIG. 1 shows an example of a flow chart illustrating this method. As shown and explained in more detail below, the method may involve receiving first data (step 102), wherein the first data represents one or more conditions of a subject's external body portion in a first time frame; receiving second data (step 104), wherein the second data is representative of the condition of the subject's external body portion in a second time frame occurring after the first time frame or reflective of how the condition is expected to evolve over time; generating a forecasted evolution of the condition (step 106); and transmitting the forecasted evolution to the subject (step 108).

Figure 4:
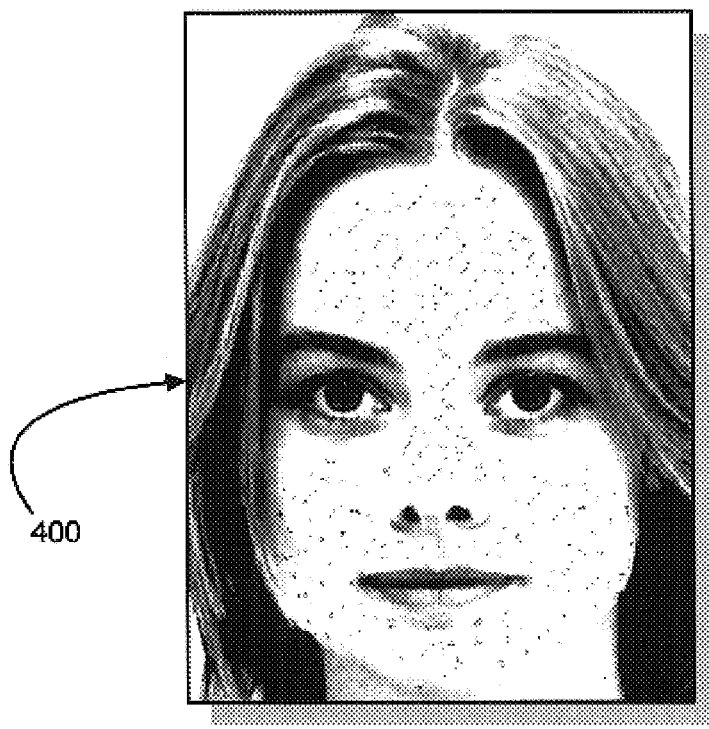
FIG. 4 illustrates an exemplary image representing first data consistent with features and principles of the invention.
Figure 5:
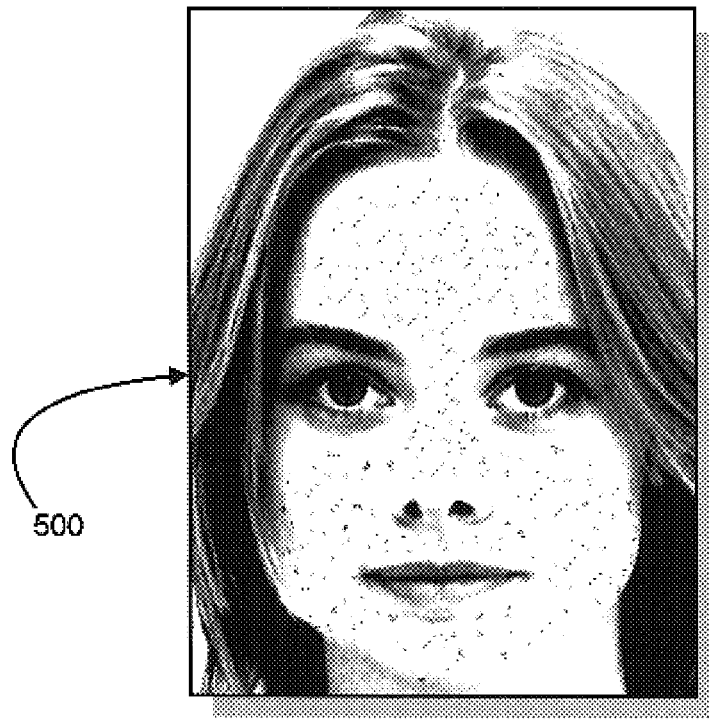
FIG. 5 illustrates an exemplary image representing second data consistent with features and principles of the invention.
Figure 6:
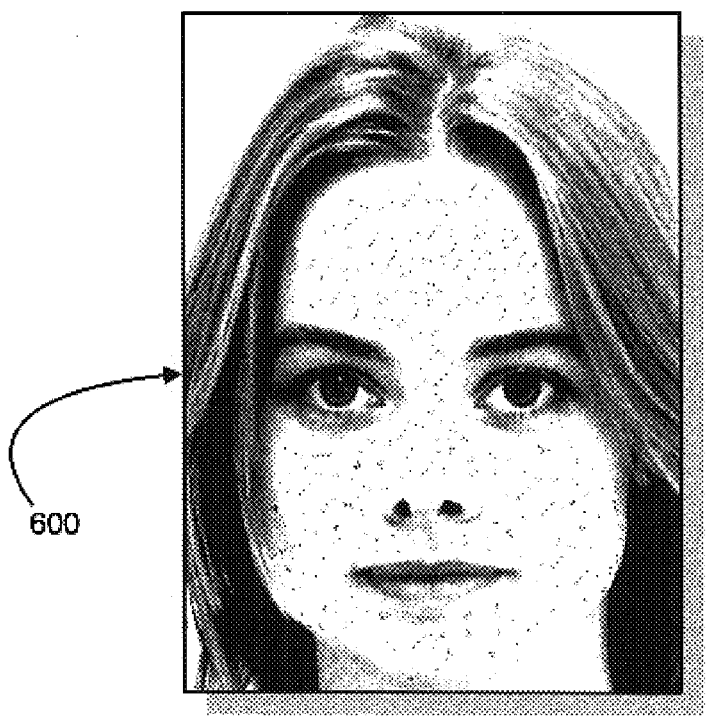
FIG. 6 illustrates an exemplary image representing a forecasted evolution consistent with features and principles of the invention.
Figure 7A:
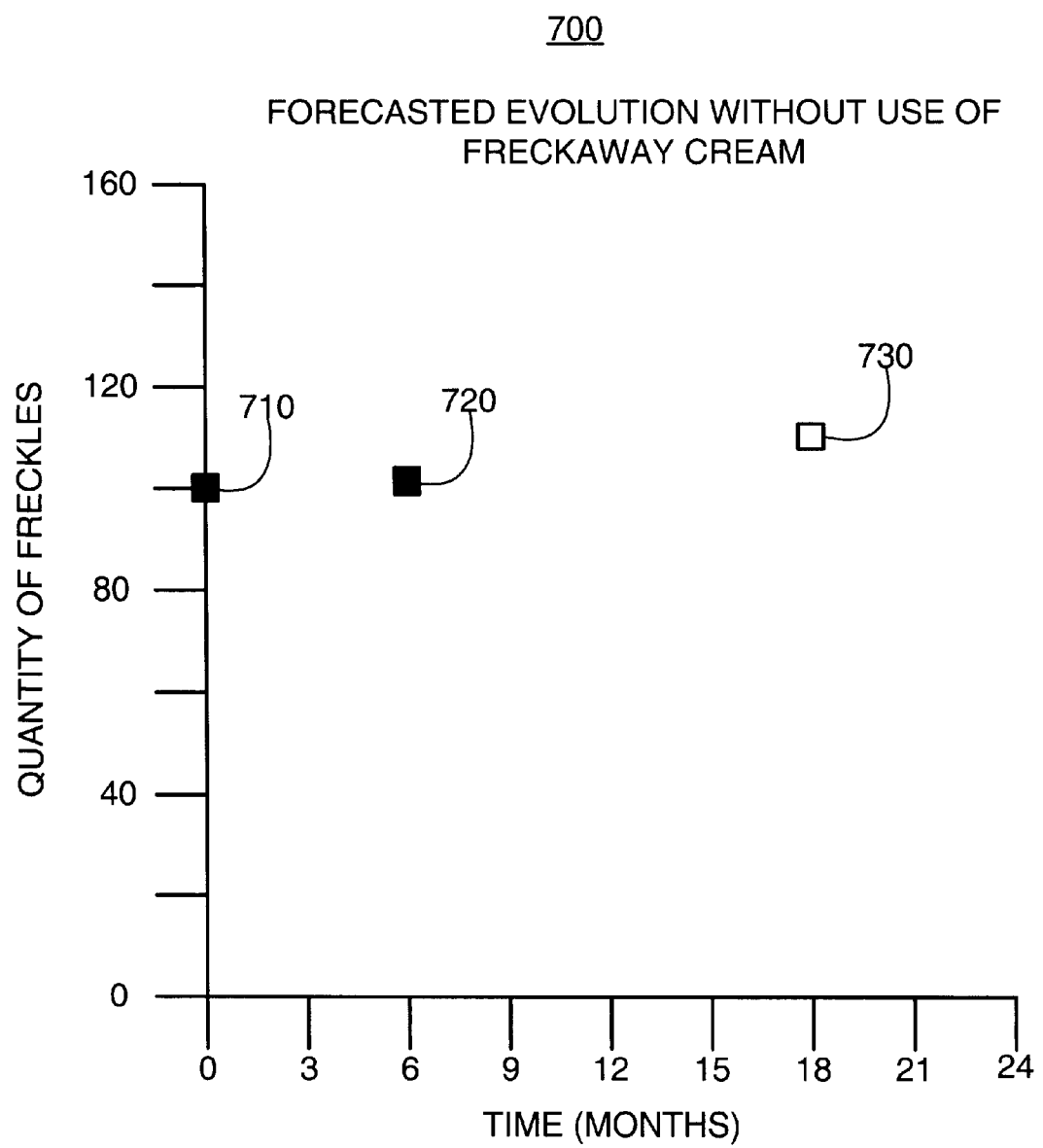
FIG. 7A illustrates a first exemplary chart representing a forecasted evolution consistent with features and principles of the invention.
Figure 7B:
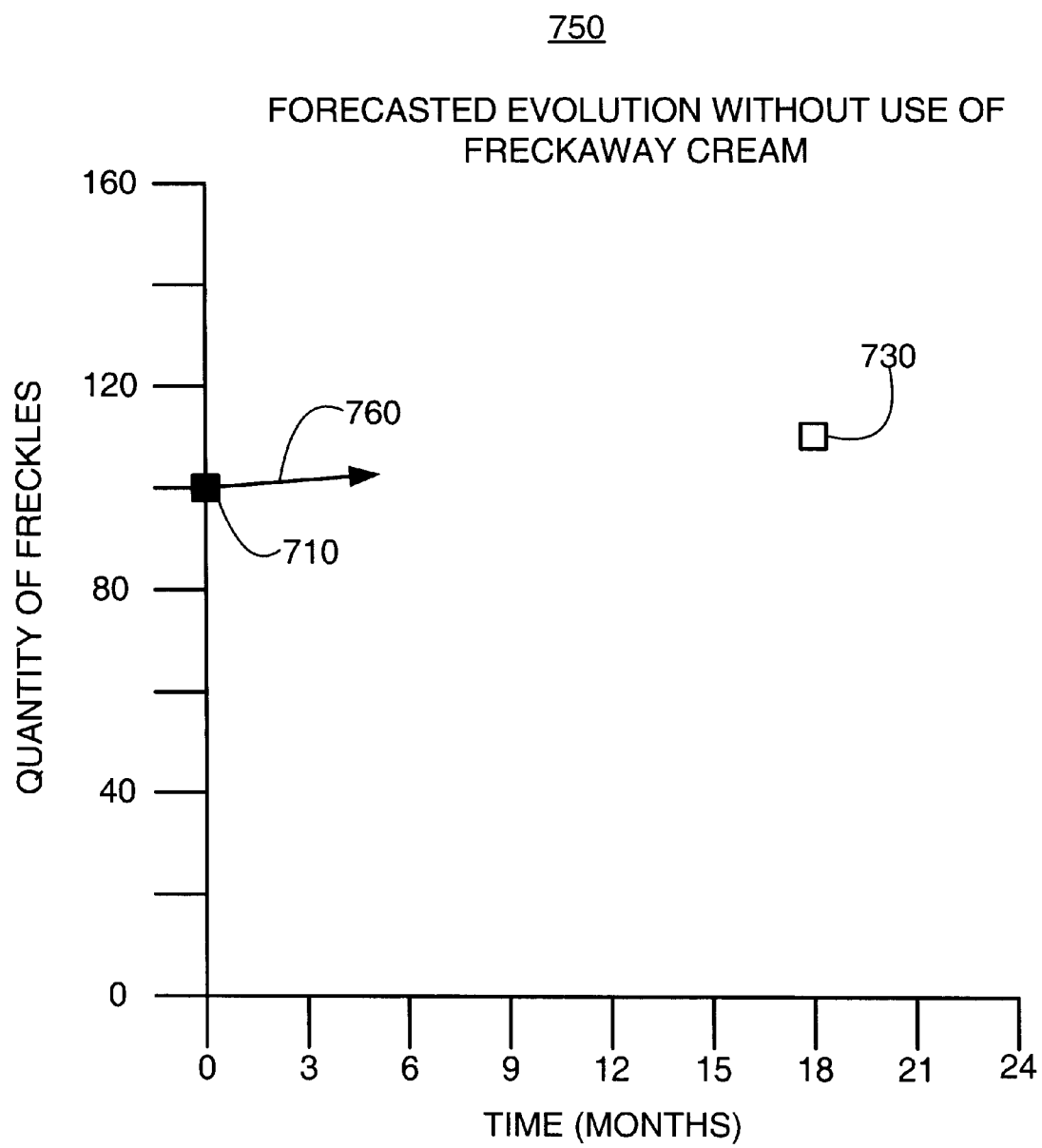
FIG. 7B illustrates a second exemplary chart representing a forecasted evolution consistent with features and principles of the invention.

FIGS. 4–7B, which are explained in more detail below, show exemplary illustrations of possible formats for the data and forecasted evolutions that might be involved in practicing the method of FIG. 1. FIGS. 4 and 5 illustrate examples of the first and second data, respectively, in the form of images; FIG. 6 shows an example of the forecasted evolution in the form of an image; and FIGS. 7A–7B show examples of the forecasted evolution in the form of charts.

In one example, the generation of the forecasted evolution may include extrapolating at least the first and second data to forecast how the condition will change in the future. In another example, the generation of the forecasted evolution may be based on database information collected via research involving a plurality of individuals having one or more conditions, wherein the information may optionally be grouped according to demographic categories. At least some aspects of the method may involve computers, software, displays, and/or other electronic devices.

The external body condition may be chosen from skin conditions, hair conditions, fingernail conditions, toenail conditions, and any other aesthetic-related conditions on a subject's external body portion. Examples of external body portions may include hair, skin, nails, face, scalp, neck, eye regions, ears, torso, arms, legs, and/or other parts of the subject's body. Examples of skin conditions may include pore size, elasticity, dryness, cellulitis, sweating, aging, wrinkles, melanoma, exfoliation, desquamation, homogeneity of color, micro-circulation, shininess, softness, smoothness, matitty, hydration, sebum production, cleanliness, irritation, redness, vasomotion, vasodilation, vasoconstriction, pigmentation, freckles, and other characteristics associated with the subject's skin. Examples of hair conditions may include keratin plug conditions, length, dryness, oiliness, dandruff, thickness, density, root conditions, split ends, hair loss, staging, and other properties related to the subject's hair. Examples of fingernail and toenail conditions may include color, gloss, strength, brittleness, thickness, hangnail, length, disease, and other characteristics related to the subject's nails.

As generally illustrated at step 102 in FIG. 1, a method consistent with the invention may include receiving first data representative of at least one condition of a subject's external body portion in a first time frame. Receiving data may involve receipt of the data through one or more networks and/or storage mediums. Networks may include public networks such as Internet, telephony networks, courier networks (e.g. postal service, United Parcel Service, Federal Express, etc.), private networks, virtual private networks, local area networks, metropolitan area networks, wide area networks, ad hoc networks, or any other mechanism for permitting communication between remote sites, regardless of whether the connection is wired or wireless. In a broader sense, data may be received physically such as in hard copy form, via mail delivery or other courier deliver. Storage mediums may include magnetic storage devices, such as floppy disks and hard drives; optical storage devices, such as compact discs and digital video discs; organic storage device; random access memory; printed media; or any other medium for storing information.

Data representative of the condition may include images (two-dimensional (2-D), three-dimensional (3-D), etc.), estimates, surveys, measurements, mechanical measurements, optical measurements, quantitative data, qualitative data, and/or other information characterizing the condition. Mechanical measurements may include the use of calipers to measure nail thickness, a corneal disc to measure skin elasticity, or any other device for making physical measurements. Optical measurements may include, for example, the use of a Woods lamp to measure a level of residue (such as porphyrine) produced by acne-causing bacteria on the subject's skin, or an infra-red lamp to measure blood circulation at the surface of the subject's skin.

FIG. 4, explained below, illustrates an example of the first data in the form of an image. Images may be obtained using image capture devices such as web cameras, film cameras, analog cameras, digital cameras, scanners, infrared imagers, ultra-sound imaging devices, or any other mechanism for acquiring a visual representation of the subject's condition. Estimates may be obtained from rough assessments provided by the subject, by other entities, by artificial intelligence, or by other sources capable of generally evaluating the condition.

The data may include an answer and/or response to at least one query prompting the subject to provide information about the subject. The query may be in the form of a question, survey, and/or prompt encouraging the subject to provide certain personal information, such as the subject's age, diet, lifestyle, physical health, vocation, environmental exposure, genetic background, information about one or more beauty products used by the subject, and/or any other relevant information.

As used herein, the term "beauty product" relates to any product that impacts either one or more conditions of an external body portion of a subject and/or causes of those conditions. Beauty products may include tangible merchandise (cosmetic, non-cosmetic, accessories, or apparel), services (beauty applications, hair styling, hair cutting, hair coloring), diagnostics, beauty regimen (e.g., a combination of merchadise and/or services), and/or advice. Examples of beauty products may include beauty products, such as treatment products, personal cleansing products, and makeup products. Beauty products may be in any form capable of being applied to an external body portion of a subject. Examples of such products include ointments, lotions, creams, gels, oils, sprays, soaps, shampoos, conditioners, scrubs, rinses, washes, etc.

As mentioned above, the received information of step 102 of FIG. 1 is representative of the condition of the external body portion at a first time frame. As used herein, the term "time frame" may relate to a particular instant in time, period of time, and/or a collection of non-contiguous instances or periods of time when data representative of the condition is initially obtained. For example, representative data relating to the condition at the first time frame may include an image of the subject's facial skin captured at one instant, a video recorded over a contiguous period, or a video of vignettes recorded over different non-contiguous durations in one period. In examples of the invention, the data could be received in step 102 at substantially the same time the data is initially captured or at a later time.

As shown in FIG. 1, the method may also include receiving second data representative of the condition of the subject's external body portion in a second time frame. The second time frame may occur completely after or partially after (e.g., overlap) the first time frame described above. The second data may or may not be similar in format to the first data. For example, the first and second data may be a photograph and an ultra-sound image, respectively, of the subject's external body portion. The second data may or not be received in the same manner as the first data. For example, the first data may be received through the Internet and the second data may be received through a floppy disk. FIG. 5, explained below, shows an example of second data in the form of an image.

Alternatively, the second data may be reflective of how the condition is expected to evolve over time. For example, the first data may represent a severity of a condition and the second data may be a mathematical model capable of predicting a future severity of the condition based on the first data. Optionally, the second data may include a vector or an empirically derived trend reflective of how the condition is expected to evolve. Second data may be derived using image processing analysis on a body image or alternatively may be derived through characteristic (physical, physiological, biological, and aesthetic) data collected from the subject.

Examples of image process techniques for deriving second data are set forth in a concurrently filed application Ser. No. 10/024,495 entitled Feature Extraction in Beauty Analysis, which is incorporated herein by reference.

In another example, one or more beauty products may have been applied to the external body portion between the first and second time frames, and such beauty products might impact the evolution of the external body portion.

As generally illustrated at step 106 in FIG. 1, the method may further include generating a forecasted evolution of the condition of the subject's external body portion based on the first and the second data. The forecasted evolution may be in the form of one or more of a diagram, graph, chart, table, index, report, graphical presentation, model, image (e.g., a 2-dimensional image and/or a 3-dimensional image), time-lapsed image, slide show, movie, video, simulation, text, or any other mechanism capable of conveying predicted changes in a condition. FIG. 6, explained below, shows an example of the forecasted evolution in the form of an image; and FIG. 7A, explained below, shows an example of the forecasted evolution in the form of a chart.

In one example, the forecasted evolution may be generated based on an assumption that a beauty product has been applied at least once to the external body portion. For example, such a forecasted evolution might illustrate how that product might improve the condition of the body portion. The method might also involve presenting the subject with information about the beauty product used as a basis for generating the forecasted evolution, as well as optional information enabling the subject to submit a purchase order for the product. In another example, the subject may be enabled to select one or more product application parameters, such as the number of assumed uses of the product, the amount of product applied, and the time period during which the product is applied, and the forecasted evolution might be generated as a function of the selected parameters.

The forecasted evolution may be generated by sending the first and second data to a data analysis node via a network; by using linear regression, mathematical models, statistics, demographic information, artificial intelligence, and/or image processing techniques, such as image morphing; and/or by comparing the first and second data with evolution data contained in a data structure, which could be configured in the form of any conventional structure for storing data.

When the image generation uses a data structure, data in the data structure may include demographic information resulting from one or more surveys, questionnaires, research projects, studies, and market analyses. Information in the data structure could be maintained in a variety of differing ways, such as by updating data in the data structure to include data relating to more individuals and/or more products. Maintaining may also include tracking and formatting the data.

When the forecasted evolution is generated through the use of artificial intelligence, there are a number of different artificial intelligence techniques that may be used. Artificial intelligence may include one or more known techniques, such as neural network, constraint program, fuzzy logic, classification, conventional artificial intelligence, symbolic manipulation, fuzzy set theory, evolutionary computation, cybernetics, data mining, approximate reasoning, derivative-free optimization, decision trees, and soft computing.

Image processing techniques may include software programs and algorithms that employ image morphing. Such techniques may be practiced on a computer, application specific integrated circuit, electronic device and/or a processor designed to forecast evolution of a condition.

As generally illustrated at step 108 in FIG. 1, the method may additionally include transmitting a forecasted evolution to a subject. Transmission may include sending the forecasted evolution to the subject via one or more of a network (described above), oral communication, visual communication, written communication, physical data carrier, and/or any other means capable of conveying information. Examples of a physical data carrier may include one or more of paper stock, an electronic data carrier, and a computer screen. In a broader sense, rather than directly sending the forecasted evolution to the subject, the transmitting might involve sending the evolution to another party who may complete transmission to the subject. For example, company ABC may prepare a printed report containing the forecasted evolution and company XYZ send the report to the subject.

In one example, the transmitting of the forecasted evolution may include transmitting computer readable instructions and/or data that could be used to form a visually perceptible representation of the forecasted evolution. Such an example, might involve transmission of data that could be used to form an image or chart, for example.

Transmitting the forecasted evolution to the subject does not necessarily require the subject to directly and/or physically receive the transmitted evolution. For example, the evolution could be transmitted to a computer which is used by the subject to view the evolution.

Although the flow chart of FIG. 1 shows receiving first data and second data (steps 102 and 104), the method might also involve receiving additional data. Such additional data may include third data representative of the condition of the subject's external body portion prior to the first time frame mentioned above. The additional data may also include data representative of the condition at various time frames before, after, overlapping with, and/or concurrent with the time frames of the other received data. The additional data may be optionally used along with the other received data to generate a forecasted evolution. In one example, at least some of the additional data received in the method might include personal information about the subject, such as the subject's age, lifestyle, beauty product use, etc. and such information could be used in generating the forecasted evolution.

In some examples, the method may include presenting information to a subject about at least one product for treating at least one condition. Presenting may be in the same form as the transmitting in the above description of the transmission of the forecasted evolution. When the method includes receiving from the subject a request to purchase the product, the receiving may be via the means employed to receive the first and second data.

The method may also include presenting information to the subject about at least one product that could be applied to an external body portion. The information may be presented when a forecasted evolution is less satisfactory than a desired threshold level. For example, if a first product has been applied to the external body portion between the first and second time frames and the forecasted evolution indicates an undesirable change in the condition, then a second product may be recommended to the subject to positively affect the evolution. The recommendation may be based on a request by the subject or automatically provided.

Figure 2:
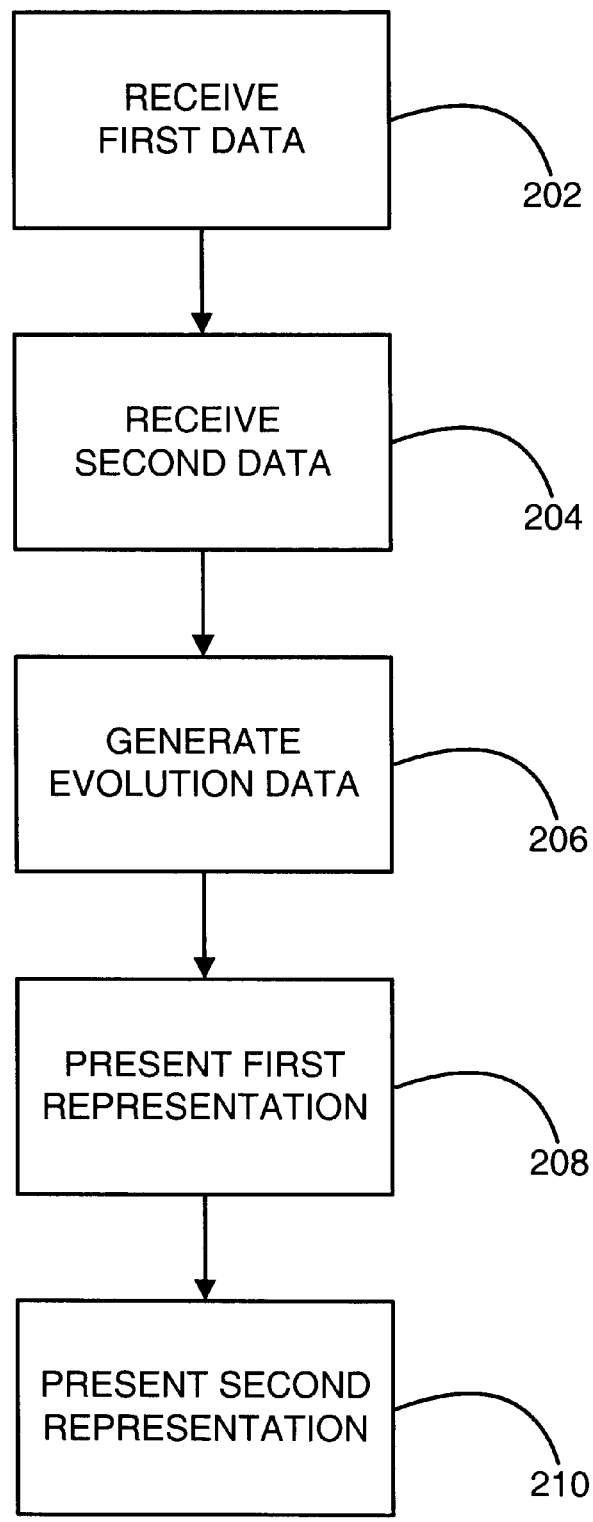
FIG. 2 illustrates a second exemplary flowchart consistent with features and principles of the invention.

The present invention may further include a method for enabling a subject to gauge effectiveness of at least one beauty product. FIG. 2 illustrates an exemplary flowchart of this method.

As illustrated in FIG. 2, the method may include receiving first data representative of one or more conditions of a subject's external body portion in a first time frame (step 202), and receiving second data representative of one or more conditions of the subject's external body portion in a second time frame occurring after the first time frame (step 204). The receiving of the first and second data could occur in the same manner as the receiving of the first and second data described above in association with FIG. 1.

In the method of FIG. 2, one or more beauty products may have been applied to the external body portion between the first and second time frame. With such an arrangement, the first data might provide information relevant in determining the status of the condition prior to application of the product and the second data might provide information relevant in determining the status of the condition after application of the product.

As shown in FIG. 2, the method may also include generating evolution data based at least in part on first and second data (step 206). The generation of evolution data may be conducted in a manner like the above-described generation of the forecast evolution.

In one example, the evolution data may be at least substantially the same as the above-described forecasted evolution. In an alternative example, the evolution data may be representative of the condition of the subject's external body portion in a time period ranging from the first time period through the second time period. Optionally, the evolution data may not include any substantial information providing a forecast of the condition beyond the second time period. In such an alternative example, the evolution data might substantially relate to the current status of the subject's external body condition.

As generally illustrated at step 208 in FIG. 2, the method may further include presenting to the subject a first representation of the evolution data. For example, the first representation may be presented as described above in association with transmission step 108 of FIG. 1. Presenting may also include causing display of images of the subject with visual cues marking conditions exhibited by the subject. Presenting may further include using image processing techniques for extracting a representation of conditions to qualify or quantify the condition.

Figure 8:
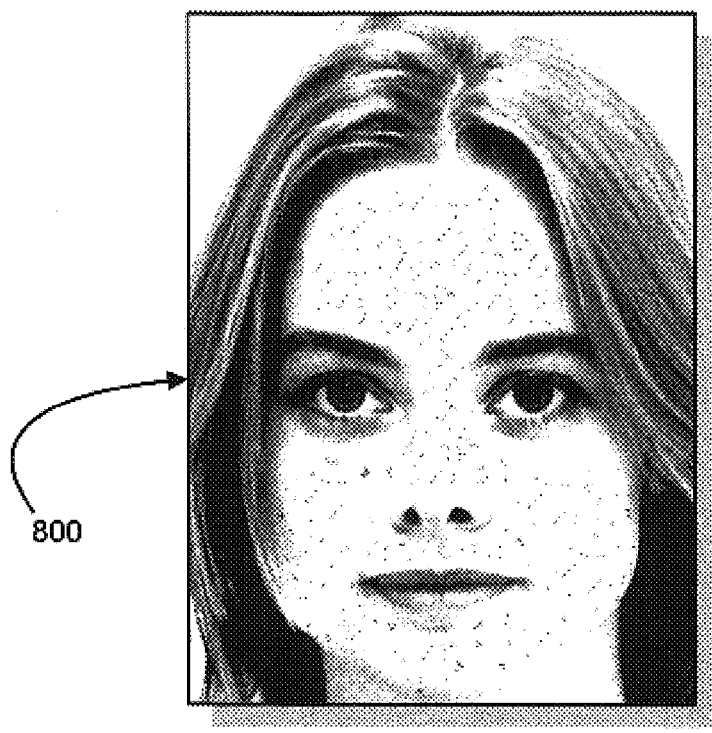
FIG. 8 illustrates an exemplary image representing an expected evolution consistent with features and principles of the invention.

Additionally, the method might also include generating an expected evolution of the condition of the external body portion. The expected evolution could be in a form like that of the forecasted evolution described in association with the method of FIG. 1. FIG. 8, described in more detail below, shows an example of an expected evolution in the form of an image; and FIG. 9, also described in more detail below, shows an example of the expected evolution in the form of a chart. The expected evolution may relate to what one would normally expect the subject's external body condition to be like when using a beauty product applied to the external body portion between the first and second time frames. For example, the expected evolution may relate to the average result that could be expected when using the beauty product. In another example, the expected evolution may relate to the minimum result that could be expected when using the beauty product.

The expected evolution may be generated in a manner like that described above in association with the generation of the forecasted evolution of FIG. 1. For example, the expected evolution may be generated based on the first data, second data, and/or the evolution data, as well as information relating to the beauty product(s) used between the first and second time frames.

Alternatively, rather than generating the expected evolution, the expected evolution may be pre-generated information stored in a data storage device. For example, the expected evolution may be based on the results of research relating to one or more beauty products.

Figure 11:
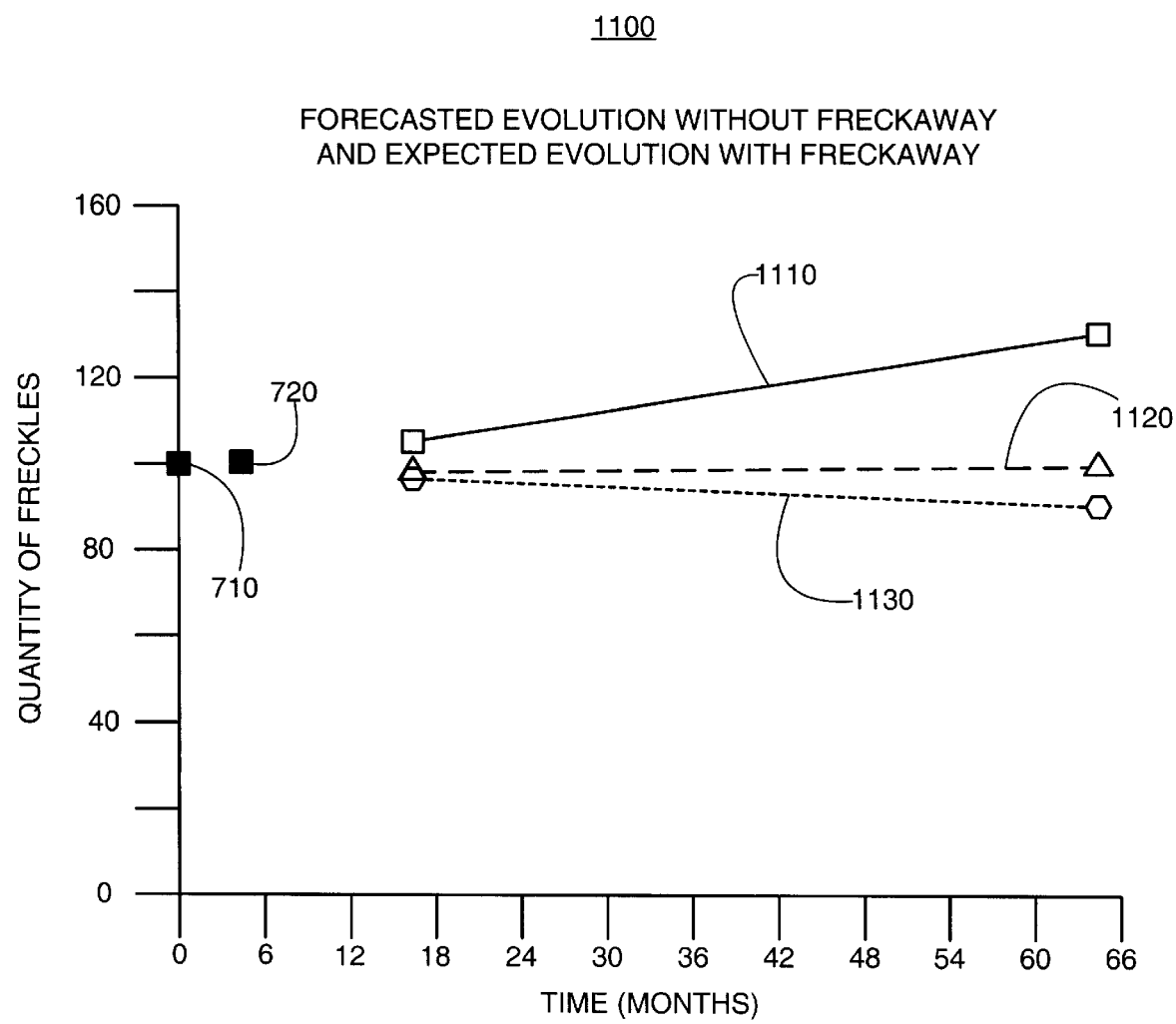
FIG. 11 illustrates an exemplary chart conjunctively presenting forecasted and expected evolutions consistent with features and principles of the invention.

As generally illustrated at step 210 in FIG. 2, the method may additionally include presenting to a subject a second representation of the expected evolution in conjunction with the presentation of the first representation of the evolution data. Both the manner of presenting and the form of the representations could be like those described in association with the transmitting of the forecasted evolution in step 108 of FIG. 1. FIGS. 10A–10H, described in more detail below, show an example of a conjunctive presentation of representations in the form of images, wherein images 400, 500, 600, and 1010 may be evolution data images and images 800, 1020, 1030, and 1040 may be expected evolution images. FIG. 11, described in more detail below, shows an example of a conjunctive presentation in the form of a chart wherein curve 1110 may represent evolution data and curves 1120 and 1130 may represent expected evolutions.

The conjunctive presentation of step 108 of FIG. 2 may be configured to permit the subject to gauge effectiveness of a beauty product applied between first and second time frames. For example, with respect to FIG. 10, a comparison between actual evolution images 400, 500, 600, and 1010 and the expected images 800, 1020, 1030, and 1040 would enable a subject to determine the effectiveness of a beauty product being used. Similarly, with regard to FIG. 11, a comparison between actual evolution curve 1110 and expected evolution curves 1120 and 1130 would enable a subject to make a determination of whether a beauty product being used is effective.

The representations of the evolution data and the expected evolution may include any form described above for the forecasted evolution of FIG. 1. In one example, where the representations are images, the first representation may be a first image forecasting an evolution of the condition over time without treatment of a beauty product; and the second representation in the form of a second image may show a expected evolution that includes the usage of a beauty product. In such an example, the evolution data and expected evolution may indicate a difference between using and not using the beauty product.

The second representation may also show an expected change based on a variation in usage of the beauty product. For example, the first representation may include an image illustrating the current and/or future state of a condition if the subject uses a beauty product once a week at moderate doses. The second representation may include an image illustrating the expected state of a condition if the subject modifies usage of a beauty product to two times a week, daily, different times of the day, various lengths of time, greater or smaller doses, combinations with one or more other products, or any other variation of usage.

Figure 3:
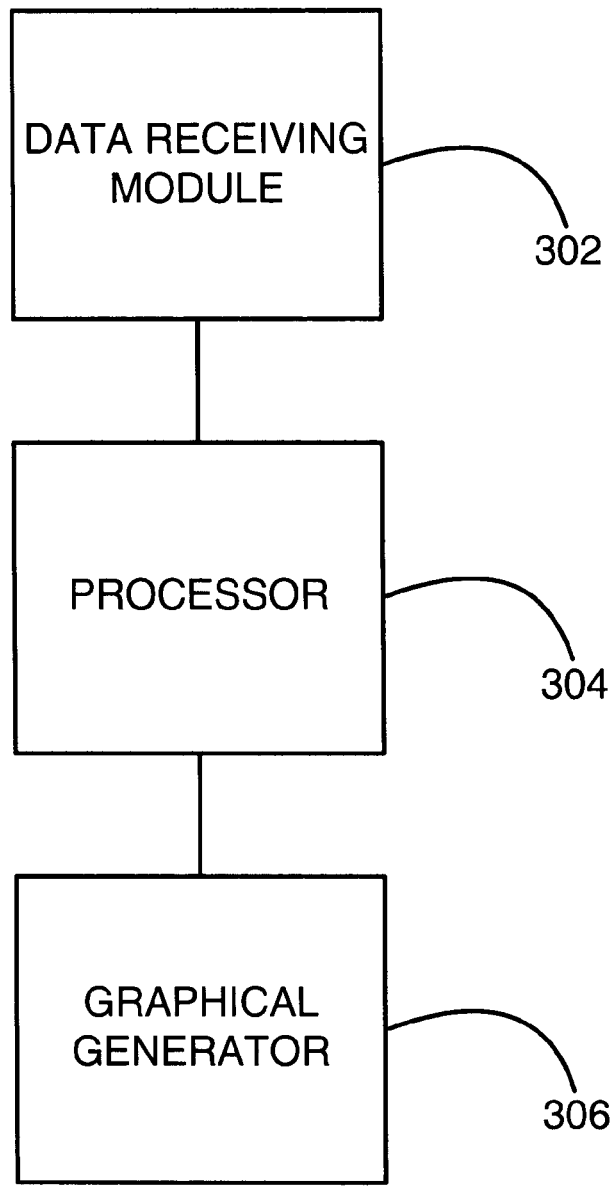
FIG. 3 illustrates an exemplary system consistent with features and principles of the invention.

Features and principles of the present invention may be implemented in system 300 of FIG. 3. System 300 may include data receiving module 302, processor 304, and graphical generator 306. Data receiving module 302 may receive the first and second data. Processor 304 may generate the forecasted evolution (step 108 of FIG. 1) and/or evolution data (step 206 of FIG. 2) based on the first and second data. Graphical generator 306 may cause generation of the forecasted evolution (step 106 of FIG. 1) and/or the conjunctive presentation of a first and second representation of an expected evolution (steps 208 and 210 of FIG. 2).

For example, the following is a description of an embodiment of the invention that may involve a beauty product, such as FreckAway cream, for reducing a condition, such as freckles, on the subject's face. In the embodiment, the data receiving module 302 may be a web camera. At a first time frame, exemplary image 400 in FIG. 4 may be captured using the web camera. At a second time frame six months later, exemplary image 500 in FIG. 5 may also be captured using the web camera. From images 400 and 500, processor 304 may generate exemplary quantitative data such as the number of freckles, the average intensity of freckles, and the average size of freckles for each image. Using the quantitative data and/or images 400 and 500, processor 304 may further generate an exemplary forecasted evolution of the freckle condition representing the freckle condition twelve months after the second time frame. The forecasted evolution may be presented by graphical generator 306 in an image representation such as exemplary image 600 in FIG. 6. As indicated by image 600, the forecasted evolution predicts approximately a five percent increase in the number and size of freckles. Alternatively, the forecasted evolution may be presented by graphical generator 306 in a diagram such as exemplary chart 700 in FIG. 7A. Data points 710 and 720 correspond to the number of freckles measured from the first and second data. Forecasted data point 730 represents a prediction of an approximately five percent increase in freckles from intial data point 710.

In another embodiment, rather than relying upon a second image as described above, the second data may be a vector reflecting how the freckles are expected to evolve over time in the absence of treatment. The vector may reflect an average expected evolution as derived from research data. The research data relied upon may be generalized or may be specific to individuals who share personal attributes with the subject (and particularly attributes known to correlate with the subject's condition).

FIG. 7B illustrates a second exemplary graph 750 also reflecting evolution over time without treatment, and being based on the first data point 710 relied upon in FIG. 7A. However, in FIG. 7B, second data is represented in the form of vector 760, which is used to project a forecasted data point 730.

Figure 9:
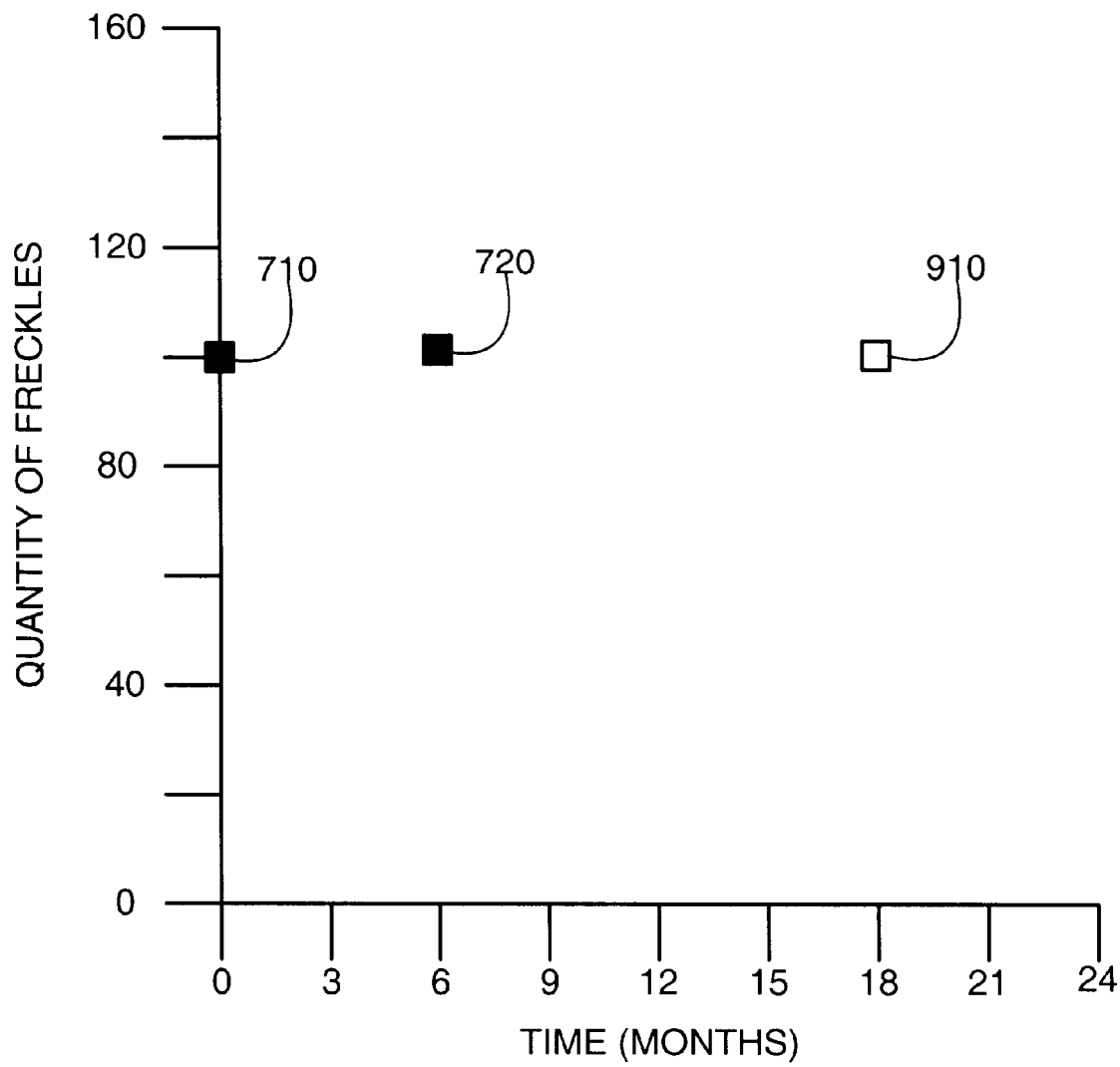
FIG. 9 illustrates an exemplary chart representing an expected evolution consistent with features and principles of the invention.

As illustrated in FIG. 9, processor 304 of FIG. 3 may in a similar manner generate an expected evolution predicting changes in the freckle condition when FreckAway cream is used. Alternatively, the expected evolution may be generated using artificial intelligence techniques, or the expected evolution might be retrieved from a data storage device without being generated, as described earlier. The expected evolution may be presented by graphical generator 306 in a graphical representation such as exemplary image 800 shown in FIG. 8, or exemplary chart 900 shown in FIG. 9. As indicated by image 800 and expected data poing 910 in chart 900, weekly use of the FreckAway cream is expected to reduce the number and size of freckles by approximately one percent.

Additionally, processor 304 may generate multiple expected evolutions for variation in usages of FreckAway cream. The multiple expected evolutions may illustrate differences in predicted changes for the freckle condition as a function of FreckleAway cream usage. Graphical generator 306 may conjunctively display representations of the forecasted and multiple expected evolutions to permit the subject to gauge the effectiveness of the FreckAway cream. FIGS. 10A–10H illustrate exemplary time-lapsed images representing the forecasted and multiple expected evolutions of the freckle condition. Images 600 and 1010 are representations of forecasted evolutions eighteen and sixty six months after the second timeframe (six months) without the use of FreckAway cream, respectively. Images 800 and 1020 are representations of expected evolutions eighteen and sixty six months after the second time frame with weekly use of FreckAway cream. Images 1030 and 1040 are representations of expected evolutions of the freckle condition eighteen and sixty six months after the second time frame with daily use of FreckAway cream. Alternatively, graphical generator 306 may conjunctively present forecasted and expected evolutions using an exemplary chart 1100 illustrated in FIG. 11. Curve 1110 is a representation of the forecasted evolution with use of FreckAway cream. Curves 1120 and 1130 are representations of the expected evolutions with weekly and daily use of FreckAway cream, respectively.

Based on the forecasted and/or expected evolutions (and possibly also the evolution data), for example, the subject may choose to purchase and use FreckAway cream. Processor 304 may be configured to allow the subject to place a purchase order for the cream over a network. If the subject deems the evaluations of the forecasted and/or expected evolutions (and possibly also the evolution data) do not meet a desired threshold level (e.g., the subject wants a greater reduction in freckles), the subject may request a recommendation for a second product to be used with or in place of the FreckAway cream. For example, processor 304 may recommend FreckErase ointment to use in combination with FreckAway cream. The recommendation may be provided regardless of whether the subject makes the request.

Figure 12:
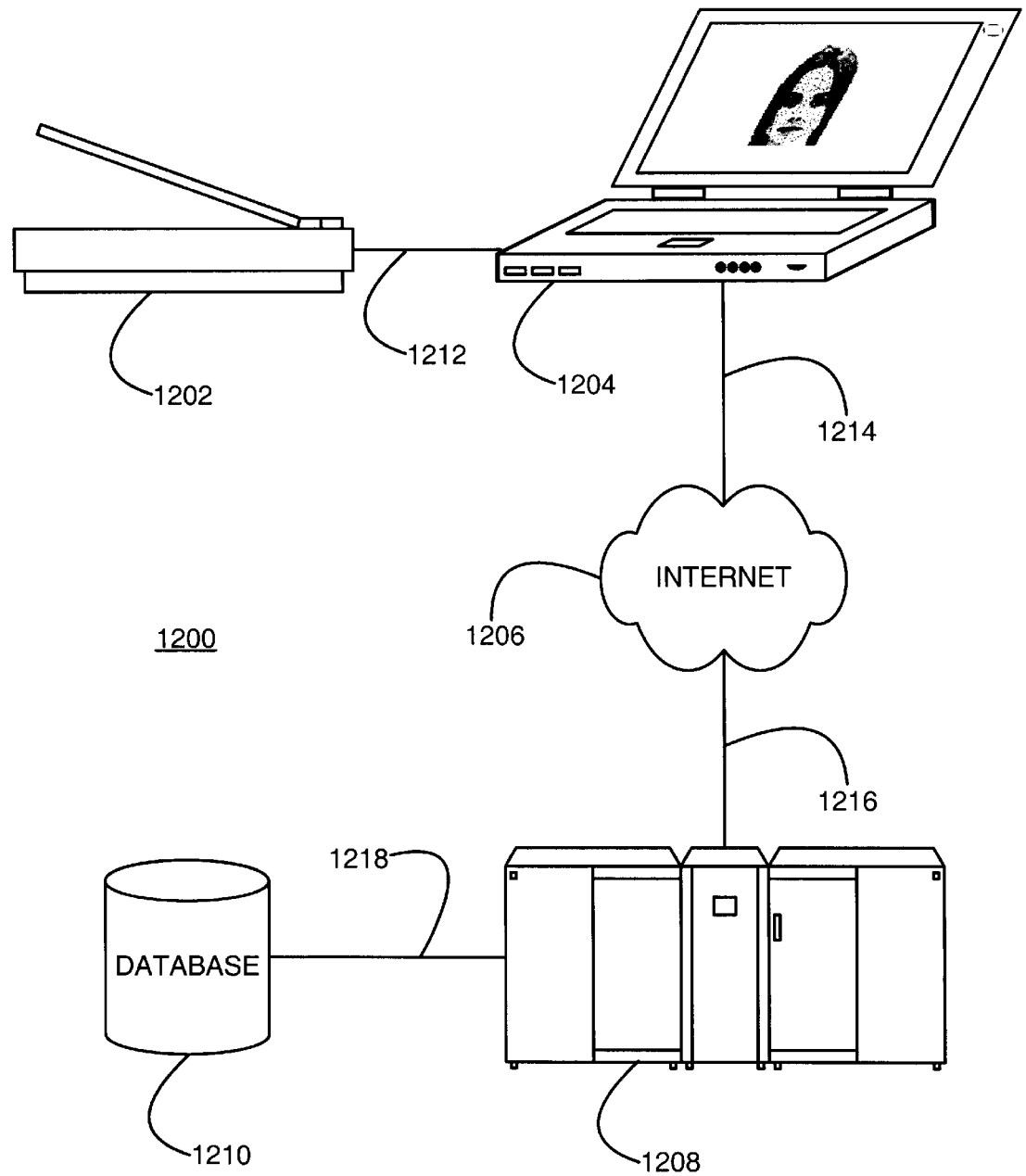
FIG. 12 illustrates an exemplary system in accordance with the features and principles of the present invention.

In yet another embodiment, features and principles consistent with the invention may be implemented in system 1200 illustrated in FIG. 12. System 1200 may include a scanner 1202, computer 1204, Internet 1206, mainframe 1208, database 1210, and four communication links 1212–1218. Scanner 1202 may be communicably connected to computer 1204 via the first communication link 1212. Computer 1204 may be communicably connected to the Internet via the second communication link 1214. The Internet 1206 may be communicably connected to mainframe 1208 via the third communication link 1216. Mainframe 1208 may be communicably connected to database 1210 via the fourth communication link 1218. The mainframe 1208 may be located at a data analysis node. The communication links may be in the form of networks (described above) or wires. For example, communication links 1212, 1214, 1216, and 1218 may be in the form of a serial cable, telephone line, local area network, and computer bus, respectively.

Scanner 1202 may be used by a subject to scan pictures of external portions of the subject taken at a first time frame from an analog camera. (Alternatively, the scanner 1202 might be used to capture an image by directly scanning a portion of the subject's body or scanning a transfer member bearing an image representative of a condition of the subject's body.) Computer 1204 may be used by the subject to send the scanned picture over the Internet 1206 to mainframe 1208. Later on, scanner 1202 may be used by the subject to scan pictures of external portions of the subject taken at a second time frame. Similarly, mainframe 1208 may receive the scanned pictures from the second time frame via the computer 1204 and Internet 1206. The scanned pictures may contain representations of a condition. Mainframe 1208 may perform image processing and use artificial intelligence to generate a forecasted evolution of the condition. Mainframe 1208 may use statistical information from database 1210 in generating the forecasted evolution. The statistical information may be from other subjects similar to the subject.

The forecasted evolution may be transmitted to computer 1204 via the Internet 1206. Computer 1204 may then present a representation of the forecasted evolution to the subject. Upon viewing the forecasted evolution, the subject may request a beauty product recommendation for changing the predicted evolution of the condition. The recommendation may be sent to mainframe 1208 via the Internet 1206. Mainframe 1208 may access product lists stored on database 1210 and use artificial intelligence to select a recommended product. Mainframe 1208 may also generate an expected evolution predicting the effectiveness of the recommended product in affecting the condition. The recommendation and expected evolution may then be sent via the Internet 1206 to computer 1204. A representation of the expected evolution and the recommendation may be presented to the subject. Based on the representation, the subject may choose to purchase and use the recommended product for the remainder of his/her lifespan.

This application may discuss beauty products in connection with use by women. However, it is to be understood that such discussions are for exemplary purposes only. It is to be understood that the invention is equally applicable to all genders, and is not necessarily limited to the beauty industry. It is also to be understood that any functional aspect of the invention can be implemented via any location in the system or network, and data software may be resident at any location either in a network, at a stand-alone site, or on media in the custody and control of a user or subject.

It is to be further understood that the physical mechanisms (e.g. hardware, software, networks, systems) for implementing the methods of the invention are many. Networks, hardware and systems can be configured in a host of ways with software and hardware functionality residing at many alternative locations. In addition, systems other than the exemplary systems disclosed might be used to implement the invention. Therefore, it is to be understood that the methods of the invention are not limited to any particular structure.

Further, methods or portions thereof can be implemented in either an electronic environment, a physical environment, or combinations thereof. Thus, for example, although one or more portions of a method may occur in an electronic environment, a "purchase" portion of the method may occur in a brick and mortar store, or vice versa.

Cross-reference to Concurrently Filed Applications and Global Definitions

This application claims priority on and incorporates by reference the following U.S. Provisional applications: Artificial Intelligence For Use In Cosmetic And Non-Cosmetic Environments, Application No. 60/325,561 (provisional filed Oct. 1, 2001); and Methods And Systems For Cosmetic And Non-Cosmetic Product Selection, Application No. 60/325,559 (provisional filed Oct. 1, 2001).

The following concurrently filed U.S. patent applications are also incorporated herein by reference: Body Image Enhancement, Ser. No. 10/024,480; Methods And Systems For Generating A Prognosis, Ser. No. 10/024,333; Historical Beauty Record, Ser. No. 10/024,622; Identification And Presentation Of Analogous Beauty Case Histories, Ser. No. 10/024,332; Interactive Beauty Analysis, Ser. No. 10/024,481; Feature Extraction In Beauty Analysis, Ser. No. 10/024,495; Simulation Of An Aesthetic Feature On A Facial Image, Ser. No. 10/024,353; Beauty Advisory System And Method, Ser. No. 10/024,496; Virtual Beauty Consultant, Ser. No. 10/024,620; Calibrating Image Capturing, Ser. No. 10/024, 334; Use Of Artificial Intelligence In Providing Beauty Advice, Ser. No. 10/024,616; Shop-In-Shop Website Construction, Ser. No. 10/024,352; Early Detection Of Beauty Treatment Progress, Ser. No. 10/024,619; Cosmetic Affinity Indexing, Ser. No. 10/024,356; Systems And Methods For Providing Beauty Guidance, Ser. No. 10/024,621; Methods And Systems Involving Simulated Application Of Beauty Products, Ser. No. 10/024,355; Customized Beauty Tracking Kit, Ser. No. 10/024,351; Analysis Using Three-Dimensional Facial Image Ser. No. 10/024,615; Body Image Templates With Pre-Applied Beauty Products, Ser. No. 10/024,482; and Image Capture Method, Ser. No. 10/024,651.

To the extent not inconsistent with the invention defined herein, definitions and terminology usage in the above-mentioned concurrently filed applications, the above-mentioned priority applications, and the following global definitions are to be considered in interpreting the language of this patent and the claims herein. Where multiple definitions are provided, they should be considered as a single cumulative definition.

The term "image" may include one or more of two-dimensional and three-dimensional representations. In certain examples consistent with the invention, a plurality of images from different perspectives may be used to construct a three-dimensional image. In a broader sense, only a single image may be used. Depending on the embodiment, the term "image" may include either a visually perceptible image or electronic image data that may be either used to construct a visually perceptible image or to derive information about the subject. The image may be a body image corresponding to an anatomical portion of the subject, and may represent, for example, the subject's entire face, or a portion of the subject's face. The image may be a detailed picture (e.g., a digital image or a photograph) of a portion of the subject's body and/or a topological plot mapping contours of a portion of subject's body. If the image is representative of an external body condition, the image could be either an actual image showing the condition or an image including symbolizations of the condition, for example. The image may be an actual or a simulated image. Simulated images may include wholly or partially generated computer images, images based on existing images, and images based on stored features of a subject.

The term "image capture device", similar terms, and terms representing structures with similar functions may include one or more of a digital camera, webcam, film camera, analog camera, digital video camera, scanner, facsimile machine, copy machine, infrared imager, ultra-sound imaging device, or any other mechanism for acquiring an image of a subject's external body condition, an image of the subject's countenance, an/or an image of the subject's skin. An ultrasonic device might provide skin thickness information, or it might create a map on an area of the external location. Thus, the term "image" as used herein may be broader than a picture. Combinations of image capture devices may be used. For example, an image captured on photographic paper using a film camera might then be scanned on a flat bed scanner to create another image.

The term "capturing (an image)", or any form thereof, refers to the use of an image capture device to acquire an image. "Capturing" may refer to the direct act of using the image capture device to acquire the image. It may also include indirect acts to promote acquisition. To this end, "capturing" may include the indirect acts of providing access to hardware, or to at least one of a client-based algorithm and a server-based algorithm for causing the image capture device to capture an image. This may be accomplished by providing a user with software to aid in the image capture process, or providing the user with access to a network location at which the software resides. Also consistent with certain embodiments of the invention, capturing may include at least one of receiving an instruction from the subject to capture an image, indicating to the subject before the image is captured, and indicating to the subject when the image is captured.

The term "image processing technique" or similar terms, may include a software program, computer, application specific integrated circuit, electronic device and/or a processor designed to identify in an image one or more characteristics, such as a skin condition. Such techniques may involve binarization, image partitioning, Fourier transforms, fast Fourier transforms (FFTs), and/or discrete cosine transforms may be performed on all or part of the image, resulting in coefficients. Based on the coefficients, conditions may be located, as known in the art. Artificial intelligence, such as fuzzy logic, neural networks, genetic programming and decision tree programming, may also be used to identify conditions. Alternatively, one or more digital filters may be passed through the image for locating specific conditions. These examples are provided for illustrative purposes with the understanding that any image processing technique may be used.

The term "network interface" or similar terms, refer to any mechanism for aiding communications between various nodes or locations in a network. A network interface may include, for example a bus, a modem, or any other input/output structure. A network interface may permit a connection to any network capable of being connected to an input and/or output module located within at least one or more of the following exemplary networks: an Ethernet network, an Internet Protocol network, a telephone network, a radio network, a cellular network, or any mechanism for permitting communication between two or more modes or remote locations. In some invention embodiments, a network interface might also included a user interface.

The term "user interface" may include at least one component such as a keyboard, key pad, mouse, track ball, telephone, scanner, microphone, touch screen, web cam, interactive voice response system (IVR), voice recognition system or any other suitable input mechanism for conveying information. A user interface may also include an input port connected by a wired, optical, or wireless connection for electromagnetic transmissions. In some embodiments, a user interface may include connections to other computer systems to receive the input commands and data therefrom. User interface may further include a data reading device such as a disk drive for receiving input data from and writing data to storage media such as magnetic and optical disks.

As used herein terms such as "external body condition", "skin condition", and "actual condition" refer to conditions of at least one of the skin, teeth, hair, eyebrows, eyelashes, body hair, facial hair, fingernails, and/or toenails, or any other externality. Examples of skin conditions may include elasticity, dryness, cellulitis, sweating, aging, wrinkles, melanoma, exfoliation, desquamation, homogeneity of color, creases, liver spots, clarity, lines, micro-circulation, shininess, softness, smoothness, tone, texture, matitty, hydration, sag, suppleness, stress, springiness, firmness, sebum production, cleanliness, translucency, luminosity, irritation, redness, vasocolation, vasomotion, vasodilation, vasoconstriction, pigmentation, freckles, blemishes, oiliness, pore distribution, pore size, moles, birthmarks, acne, blackheads, whiteheads, pockmarks, warts, pustules, boils, blisters, marks, smudges, specks, psoriasis and other characteristics associated with the subject's skin. Examples of hair conditions may include keratin plug, length, dryness, oiliness, dandruff, pigmentation, thickness, density, root conditions, split ends, hair loss, hair thinning, scales, staging, cleanliness and other properties related to the subject's hair. Examples of fingernail and toenail conditions may include onychomycosis, split nails, delaminating, psoriasis, brilliancy, lines, spots, coloration, gloss, strength, brittleness, thickness, hangnail, length, disease, and other characteristics related to the subject's nails. Other conditions may include, for example, size and proportion of facial features, teeth discoloration, and any other aesthetic-related or physical, physiological, or biological conditions of the user.

"Enabling", "facilitating", and "causing" an action refer to one or more of a direct act of performing the action, and any indirect act of encouraging or being an accessory to the action. Thus, the terms include partnering or cooperating with an entity who performs the action and/or referring commerce to or having commerce referred from an entity who performs the action. Other examples of indirect activity encompassed within the definitions of "enabling", "facilitating", and "causing" may include providing a subject with one or more of tools to knowingly aid in performing the action, providing instructions on how to perform the action, providing prompts or cues to perform the action, or expressly encouraging performance of the action. Indirect activity may also include cooperating with an entity who either directly performs the action or who helps another perform the action. Tools may include software, hardware, or access (either directly, through hyperlink, or some other type of cooperation or partnering) to a network location (e.g., web site) providing tools to aid in performing the action. Thus, phrases such as "enabling access" and "enabling display" do not necessary require that the actor actually access or display anything. For example, the actor may perform the enabling function by affiliating with an entity who performs the action, or by providing instructions, tools, or encouragement for another to do the accessing and displaying.

Forms of the word "displaying" and like terms may also include indirect acts such as providing content for transmission over a network to a display device, regardless of whether the display device is in the custody or control of the sender. Any entity in a chain of delivering information for display performs an act of "displaying", as the term is used herein.

Likewise, the term "providing" includes direct and indirect activities. For example, providing access to a computer program may include at least one of providing access over a network to the computer program, and creating or distributing to the subject a computer program configured to run on the subject's workstation or computer. For example, a first party may direct network traffic to (either through electronic links or through encouragement to visit) a server or web site run by a second party. If the second party maintains a particular piece of software thereon, then it is to be understood that within the meaning of "providing access" as used herein, the first party is said to provide access to the particular software. Or if the first party directs a subject to a second party who in turn ships the particular software to the user, the first party is said to provide the user with access to the particular software. (Of course, in both of the above instances, the second party would also be providing access within the meaning of the phrase as used herein.) "Receiving" may include at least one of acquisition via a network, via verbally communication, via electronic transmission, via telephone transmission, in hard-copy form, or through any other mechanism enabling reception. In addition, "receiving" may occur either directly or indirectly. For example, receipt may occur through a third party acting on another party's behalf, as an agent of another, or in concert with another. Regardless, all such indirect and direct actions are intended to be covered by the term "receiving" as used herein. A received request, for example, may take one of many forms. It may simply be a checked box, clicked button, submitted form or oral affirmation. Or it might be a typed or handwritten textual request. Receiving may occur through an on-line interest form, e-mail, facsimile, telephone, interactive voice response system, or file transfer protocol transmitted electronically over a network at a web site, an internet protocol address, or a network account. A request may be received from a subject for whom information is sought, or an entity acting on the subject's behalf. "Receiving" may involve receipt directly or indirectly through one or more networks and/or storage mediums. Receipt may occur physically such as in hard copy form, via mail delivery or other courier delivery.

Forms of the word "maintain" are used broadly to include gathering, storing, accessing, providing access to, or making something available for access, either directly or indirectly. For example, those who maintain information include entities who provide a link to a site of a third party where the information is stored.

Consistent with the concepts set forth above, all other recited actions such as, for example, obtaining, determining, generating, selecting, applying, simulating, presenting, etc, are inclusive of direct and indirect actions. Thus, for purposes of interpreting the following claims, an entity performs a recited action through either direct or indirect activity. Further examples of indirect activity include sending signals, providing software, providing instructions, cooperating with an entity to have the entity perform the action, outsourcing direct or indirect actions, or serving in any way as an accessory to the specified action.

The term "product" is used genericly refer to tangible merchandise, goods, services, and actions performed. A "beauty product," "beauty care product," "cosmetic product" or similar terms, refer to products (as defined above) for effecting one or more external body conditions, such as conditions of the skin, hair and nails. Examples of tangible merchandise forms of beauty products include cosmetic goods, such as treatment products, personal cleansing products, and makeup products, in any form (e.g., ointments, creams, gels, sprays, supplement, ingesta, inhalants, lotions, cakes, liquids, and powders.)

Examples of services forms of beauty products include hair styling, hair cutting, hair coloring, hair removal, skin treatment, make-up application, and any other offering for aesthetic enhancement. Examples of other actions performed include massages, facial rubs, deep cleansings, applications of beauty product, exercise, therapy, or any other action effecting the external body condition whether performed by a professional, the subject, or an acquaintance of the subject.

The following is exemplary and non-exhaustive listing of a few beauty products—scrubs, rinses, washes, moisturizers, wrinkle removers, exfoliates, toners, cleansers, conditioners, shampoos, cuticle creams, oils, and antifungal substances, anti-aging products, anti-wrinkle products, anti-freckle products, skin conditioners, skin toners, skin coloring agents, tanners, bronzers, skin lighteners, hair coloring, hair cleansing, hair styling, elasticity enhancing products, agents, blushes, mascaras, eyeliners, lip liners, lipsticks, lip glosses, eyebrow liners, eye shadows, nail polishes, foundations, concealers, dental whitening products, cellulite reduction products, hair straighteners and curlers, and weight reduction products. A beauty care treatment regimen may involve the administration of one or more products, as defined above.

The terms "beauty advice", "beauty guidance", and similar terms are used interchangeably to refer to the provision of beauty related information to a subject. Advice or guidance includes one or more of beauty product recommendations (e.g., cosmetic product recommendations for products to treat conditions the subject is prompted to evaluate), remedial measures, preventative measures, predictions, prognoses, price and availability information, application and use information, suggestions for complementary products, lifestyle or dietary recommendations, or any other information intended to aid a subject in a course of future conduct, to aid a subject in understanding past occurrences, to reflect information about some future occurrences related to the subject's beauty or to aid a subject in understanding beauty products, as defined above.

The term "network" may include a public network such as the Internet or a telephony network, a private network, a virtual private network, or any other mechanism for enabling communication between two or more nodes or locations. The network may include one or more of wired and wireless connections. Wireless communications may include radio transmission via the airwaves, however, those of ordinary skill in the art will appreciate that various other communication techniques can be used to provide wireless transmission including infrared line of sight, cellular, microwave, satellite, blue-tooth packet radio and spread spectrum radio. Wireless data may include, but is not limited to, paging, text messaging, e-mail, Internet access and other specialized data applications specifically excluding or including voice transmission.

In some instances consistent with the invention, a network may include a courier network (e.g. postal service, United Parcel Service, Federal Express, etc.). Other types of networks that are to be considered within the scope of the invention include local area networks, metropolitan area networks, wide area networks, ad hoc networks, or any mechanism for facilitating communication between two nodes or remote locations.

"Artificial intelligence" (AI) is used herein to broadly describe any computationally intelligent systems that combine knowledge, techniques, and methodologies. An AI engine may be any system configured to apply knowledge and that can adapt itself and learn to do better in changing environments. Thus, the AI engine may employ any one or combination of the following computational techniques: neural network, constraint program, fuzzy logic, classification, conventional artificial intelligence, symbolic manipulation, fuzzy set theory, evolutionary computation, cybernetics, data mining, approximate reasoning, derivative-free optimization, decision trees, or soft computing. Employing any computationally intelligent techniques, the AI engine may learn to adapt to unknown or changing environment for better performance. AI engines may be implemented or provided with a wide variety of components or systems, including one or more of the following: central processing units, co-processors, memories, registers, or other data processing devices and subsystems.

AI engines may be trained based on input such as product information, expert advice, user profile, or data based on sensory perceptions. Using input an AI engine may implement an iterative training process. Training may be based on a wide variety of learning rules or training algorithms. For example, the learning rules may include one or more of the following: back-propagation, real-time recurrent learning, pattern-by-pattern learning, supervised learning, interpolation, weighted sum, reinforced learning, temporal difference learning, unsupervised learning, or recording learning. As a result of the training, AI engine may learn to modify its behavior in response to its environment, and obtain knowledge. Knowledge may represent any information upon which AI engine may determine an appropriate response to new data or situations. Knowledge may represent, for example, relationship information between two or more products. Knowledge may be stored in any form at any convenient location, such as a database.

Since AI engine may learn to modify its behavior, information describing relationships for a universe of all combinations of products may not need to be maintained by the AI engine or any other component of the system.

"Personal information", "subject specific information", "user specific information", "user profile", "personal characteristics", "personal attributes", "profile information", and like terms (collectively referred to in this section as "personal information") may broadly encompass any information about the subject or user. Such information may, for example, fall within categories such as physical characteristics, fashion preferences, demographics, nutritional information, cosmetic usage information, medical history information, environmental information, beauty product usage information, lifestyle, and may include information such as name; age; birth date; height; weight; ethnicity; eating habits; vacation patterns; geographic location of the individual's residence, location, or work; work habits; sleep habits; toiletries used; exercise habits; relaxation habits; beauty care habits; smoking and drinking habits; sun exposure habits; use of sunscreen; propensity to tan; number of sunburns and serious sunburns; dietary restrictions; dietary supplements or vitamins used; diagnosed conditions affecting the external body, such as melanoma; an image, such as a picture or a multimedia file of the subject; facial feature characteristics; family history information such as physical characteristics information about relatives of the subject (e.g., premature balding, graying, wrinkles, etc.); external body condition (as defined previously); color preferences, clothing style preferences, travel habits; entertainment preferences; fitness information; adverse reactions to products, compounds, or elements (e.g., sun exposure); body chemistry, use of prior beauty care products and their effectiveness; purchasing, shopping, and browsing habits; hobbies; marital status; whether the subject is a parent; country of residence; region of residence; birth country and region; religious affiliation; political affiliation; whether the subject is an urban dweller suburban dweller or rural area dweller; size of urban area in which the subject lives; whether the subject is retired; annual income, sexual preference, or any other information reflecting habits, preferences, or affiliations of the subject.

Personal information may also include information electronically gleaned by tracking the subject's electronic browsing or purchasing habits, or as the result of cookies maintained on the subject's computer, responses to surveys, or any other mechanism providing information related to the subject. In addition, personal information may be gathered through non-electronic mechanisms such as hard copy surveys, personal interviews, or consumer preference polls.

"Complementary" and "complementary product" refers to one or more of physical, physiological, biologically, and aesthetic compatibility. A product may be complementary with one or more of another product, a group of products, or a subject. In that latter instance, whether a product is considered "complementary" may be a function of personal information of the subject. Thus, for example a product may be complementary if it is unlikely to cause an adverse allergic reaction; if it physically blends well with another product; or if it is aesthetically consistent with the subject or one or more other products. Aesthetic compatibly may refer to the fact that two products are aesthetically appealing (or do not clash) when worn together. The identification of a complementary product may also be based on product characteristics, user preferences, survey data, or expert advice.

As used herein, the words "may" and "may be" are to be interpreted in an open-ended, non-restrictive manner. At minimum, "may" and "may be" are to be interpreted as definitively including structure or acts recited. Further, the word "or" is to be interpreted in the conjunctive and the disjunctive.

While flow charts presented herein illustrate a series of sequential blocks for exemplary purposes, the order of blocks is not critical to the invention in its broadest sense. Further, blocks may be omitted and others added without departing from the spirit of the invention. Also, the invention may include combinations of features described in connection with differing embodiments.

Although a focus of the disclosure may be on server-side methods, it is nevertheless to be understood that the invention includes corresponding client-side methods, software, articles of manufacture, and computer readable media, and that computer readable media can be used to store instructions for some or all of the methods described herein. Further, it is to be understood that disclosed structures define means for implementing the functionality described herein, and that the invention includes such means for performing the disclosed functions.

In the foregoing Description of Exemplary Embodiments, various features are grouped together in a single embodiment for purposes of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Description of the Exemplary Embodiments, with each claim standing on its own as a separate embodiment of the invention.

What is claimed is:

1. A method for predicting evolution of at least one condition of an external body portion of a subject, the method comprising:
   receiving first data, wherein the first data is representative of at least one condition of an external body portion of a subject in a first time frame;
   receiving second data, wherein the second data is representative of the at least one condition of the external body portion of the subject in a second time frame occurring after the first time frame;
   generating, based on the first data and the second data, a forecasted evolution of the at least one condition of the external body portion of the subject; and
   transmitting to the subject the forecasted evolution.

2. The method of claim 1, wherein each of the first data and the second data is chosen from quantitative data and qualitative data.

3. The method of claim 1, further comprising receiving third data, wherein the third data is representative of the at least one condition of external body portion of the subject prior to the first time frame.

4. The method of claim 1, further comprising instructing the subject to use at least one cosmetic product between the first time frame and the second time frame.

5. The method of claim 4, wherein the at least one product is predicted to impact evolution of the at least one condition of the external body portion of the subject.

6. The method of claim 1, wherein the at least one condition is a skin condition chosen from pore size, elasticity, dryness, cellulitis, sweating, aging, wrinkles, melanoma, exfoliation, desquamation, homogeneity of color, micro-circulation, shininess, softness, smoothness, matitty, hydration, sebum production, cleanliness, irritation, redness, vasomotion, vasodilation, vasoconstriction, pigmentation, and freckles.

7. The method of claim 1, wherein the at least one condition is a hair condition chosen from keratin plug conditions, length, dryness, oiliness, dandruff, thickness, density, root conditions, split ends, hair loss, and staging.

8. The method of claim 1, wherein the at least one condition is chosen from fingernail conditions and toenail conditions.

9. The method of claim 1, wherein the forecasted evolution is based, at least in part, on an assumption that a product is applied at least once to the external body portion.

10. The method of claim 9, wherein the forecasted evolution is a function of at least one of a number of assumed uses of the product, an amount of the product applied, and a time period during which the product is applied.

11. The method of claim 1, further comprising presenting to the subject information about at least one product for treating the at least one condition.

12. The method of claim 11, further comprising receiving from the subject a request to purchase the at least one product.

13. The method of claim 1, wherein at least one first product is applied to the external body portion between the first time frame and the second time frame, and wherein the method further comprises presenting to the subject information about at least one second product to be applied to the external body portion.

14. The method of claim 13, wherein presenting the subject information about at least one second product occurs when the forecasted evolution is less satisfactory than a threshold level of satisfaction.

15. The method of claim 1, wherein the forecasted evolution is provided in the form of an image represented in at least two dimensions.

16. The method of claim 1, wherein the forecasted evolution is provided in the form of an image.

17. The method of claim 1, wherein each of the first data and the second data is chosen from a two-dimensional image, a three-dimensional image, a scanned image, and a representation of one of a mechanical measurement and an optical measurement.

18. The method of claim 17, wherein at least one of the first data and the second data further comprises an answer to at least one query about the subject.

19. The method of claim 1, wherein transmitting to the subject the forecasted evolution comprises transmitting to the subject the forecasted evolution on a physical data carrier.

20. The method of claim 19, wherein the physical data carrier is chosen from paper stock, an electronic data carrier, and a computer screen.

21. The method of claim 1, wherein generating comprises sending the first data and the second data to a data analysis node via a network.

22. The method of claim 1, wherein receiving of the first data and receiving of the second data occurs via a network, and wherein transmitting the forecasted evolution comprises sending the forecasted evolution to the subject via the network.

23. The method of claim 1, wherein generating comprises comparing the first data and the second data with evolution data contained in a data structure.

24. The method of claim 23, further comprising maintaining the data structure containing the evolution data.

25. The method of claim 1, wherein transmitting the forecasted evolution comprises transmitting to the subject a first graphical representation showing the forecasted evolution, and wherein the method further comprises transmitting to the subject a second graphical representation showing expected evolution of the at least one condition.

26. The method of claim 25, wherein the expected evolution relates to assumed application of a beauty product.

27. The method of claim 25, wherein the subject is enabled to view the first and second graphical representations in conjunction with one another.

28. The method of claim 1, wherein generating a forecasted evolution comprises generating a forecasted evolution that is a function of parameters, selected by the subject, relating to the application of a product to the external body portion.

29. The method of claim 1, wherein receiving first data comprises receiving first data in a first format and a first manner, and wherein receiving second data comprises receiving second data in a second format and a second manner, the first format and manner being different from the second format and manner.

30. A method for enabling a subject to gauge effectiveness of at least one beauty product, the method comprising:
  receiving first data, wherein the first data is representative of at least one condition of an external body portion of a subject in a first time frame;
  receiving second data, wherein the second data is representative of the at least one condition of the external body portion of the subject in a second time frame occurring after the first time frame, and wherein at least one beauty product is applied to the external body portion between the first time frame and the second time frame;
  generating evolution data based at least in part on the first and the second data;
  presenting the subject a first representation of the evolution data; and
  presenting the subject, in conjunction with the first representation, a second representation of an expected evolution of the at least one condition, the conjunctive presentation of the first and second representations being configured to permit the subject to gauge effectiveness of the beauty product applied between the first and second time frames.

31. The method of claim 30, wherein each of the first representation and the second representation is a graphical representation.

32. The method of claim 30, wherein each of the first representation and the second representation comprises a plurality of time-lapsed images.

33. The method of claim 32, wherein the time-lapsed images are displayed in one of a slide show format and a movie format.

34. The method of claim 30, wherein the at least one condition is a skin condition chosen from pore size, elasticity, dryness, cellulitis, sweating, aging, wrinkles, melanoma, exfoliation, desquamation, homogeneity of color, micro-circulation, shininess, softness, smoothness, matitty, hydration, sebum production, cleanliness, irritation, redness, vasomotion, vasodilation, vasoconstriction, pigmentation, and freckles.

35. The method of claim 30, wherein the at least one condition is a hair condition chosen from keratin plug conditions, length, dryness, oiliness, dandruff, thickness, density, root conditions, split ends, hair loss, and staging.

36. The method of claim 30, wherein the at least one condition is chosen from conditions and toenail conditions.

37. The meted of claim 30, wherein the expected evolution is a function of at least one of a number of assumed uses of to product, an amount of the product applied, and a time period during which to product is applied.

38. The method of claim 30, further comprising transmitting to the subject information about at least one second product fir treating to at least one condition.

39. The meted of claim 38, further comprising receiving from the subject a request to purchase the at least one second product.

40. The meted of claim 38, wherein transmitting information about at least one second product occurs when to effectiveness of the beauty product is less satisfactory than a threshold level of satisfaction.

41. The meted of claim 30, wherein each of the first representation and the second representation is provided in the form of an image represented in at least two dimensions.

42. The method of claim 30, wherein each of the first representation and the second representation is provided in the form of an image.

43. The method of claim 30, wherein each of the first data and the second data is chosen from a two-dimensional image, tree-dimensional image, a scanned image, and a representation of one of a mechanical measurement and an optical measurement.

44. The method of claim 42, wherein at least one of the first data and the second data further comprises an answer to at least one query about the subject.

45. The method of claim 30, wherein at least one of presenting the subject the first representation and presenting the subject the second representation comprises presenting the subject a representation on a physical data carrier.

46. The method of claim 45, wherein the physical data carrier is chosen from paper stock, an electronic data carrier, and a computer screen.

47. The method of claim 30, wherein receiving of the first data and receiving of the second data occurs via a network, and wherein presenting the subject the first representation and presenting the subject the second representation comprises sending the representations to the subject via the network.

48. The method of claim 30, further comprising generating the second representation.

49. The method of claim 48, wherein the second representation is generated based on expected evolution data contained in a data structure.

50. The method of claim 49, further comprising maintaining the data structure containing the expected evolution data.

51. The method of claim 49, wherein the expected evolution data relates to assumed application of the beauty product.

52. The method of claim 30, wherein presenting the subject with a second representation comprises presenting the subject with a second representation reflecting an expected change to the at least one condition based on a variation in usage of the beauty product.

53. A system for enabling a subject to gauge effectiveness of a beauty product, the system comprising:
- a data receiving module for receiving first data and second data, wherein the first data is representative of at least one condition of an external body portion of a subject in a first time frame, the second data is representative of the at least one condition of the external body portion of the subject in a second time frame occurring after the first time frame, and at least one beauty product is to the external body portion between the first time frame and the second time frame;
- a processor for generating evolution data based on the first and second data, the evolution data representing evolution of the external condition between the first and second time frames; and
- a graphical generator for causing the subject to be presented conjunctively with a first representation of the evolution data and a second representation of an expected evolution of the at least one condition, the conjunctive presentation of the first and second representations being configured to permit the subject to gauge effectiveness of the beauty product applied between the first and second time frames.

54. A method for predicting evolution of at least one condition of an external body portion of a subject, the method comprising:
- receiving first data, wherein the first data is representative of the at least one condition;
- receiving second data, reflective of how the at least one external body condition is expected to evolve over time, wherein the second data is derived using characteristic data collected from the subject;
- generating, based on the first data and the second data, a forecasted evolution of the at least one condition; and
- transmitting to the subject the forecasted evolution.

55. The method of claim 54, conducted, at least in part in a network environment, wherein receiving the first and the second data occurs via a network and in at least one location remote from a location of the subject, and wherein during transmitting, the forecasted evolution is sent to the subject over the network.

56. A system for enabling a subject to gauge effectiveness of a beauty product, the system comprising:
- a data receiving module for receiving first data and second data, wherein the first data is representative of at least one condition of an external body portion of a subject and the second data is reflective of how the at least one external body condition is expected to evolve over rime with at least one application of a beauty product;
- a processor for generating evolution data based on the first and second data, the evolution data representing evolution of the external condition; and
- a graphical generator for causing the subject to be presented conjunctively with a first representation of the evolution data and a second representation of an expected evolution of the at least one condition, the conjunctive presentation of the first and second representations being configured to permit the subject to gauge effectiveness of the beauty product.

* * * * *

UNITED STATES PATENT AND TRADEMARK OFFICE
CERTIFICATE OF CORRECTION

PATENT NO. : 6,761,697 B2
DATED : July 13, 2004
INVENTOR(S) : Gilles Rubinstenn et al.

It is certified that error appears in the above-identified patent and that said Letters Patent is hereby corrected as shown below:

Column 22,
Line 13, insert -- fingernail -- between "from" and "conditions".
Lines 14, 21, 24 and 28, "meted" should read -- method --.
Line 16, "of to product" should read -- of the product --.
Line 17, "which to product" should read -- which the product --.
Line 20, "fr" should read -- for --.
Line 20, "to at least" should read -- the at least --.
Line 25, "when to" should read -- when the --.
Line 39, "claim 42" should read -- claim 43 --.

Column 23,
Line 13, insert -- applied -- between "is" and "to".

Signed and Sealed this

Twenty-first Day of December, 2004

JON W. DUDAS
*Director of the United States Patent and Trademark Office*